(12) United States Patent
Grant et al.

(10) Patent No.: US 6,277,118 B1
(45) Date of Patent: Aug. 21, 2001

(54) EXTERNAL FIXATOR INCLUDING AN ANGULAR CORRECTION MODULE AND RELATED METHOD

(75) Inventors: Alfred D. Grant, Harrison, NY (US); Kirk J. Bailey, Andover; Milton R. Torres, Jr., Belle Mead, both of NJ (US)

(73) Assignee: Electro-Biology, Inc., Parsippany, NJ (US)

( * ) Notice: Subject to any disclaimer, the term of this patent is extended or adjusted under 35 U.S.C. 154(b) by 0 days.

(21) Appl. No.: 09/495,204

(22) Filed: Jan. 31, 2000

(51) Int. Cl.[7] ................................................. A61B 17/64
(52) U.S. Cl. ............................................. 606/54; 606/59
(58) Field of Search .................................. 606/53, 54, 55, 606/56, 57, 58, 59

(56) References Cited

U.S. PATENT DOCUMENTS

| | | |
|---|---|---|
| 2,251,209 | 7/1941 | Stader . |
| 2,333,033 | 10/1943 | Mraz . |
| 2,391,537 | 12/1945 | Anderson . |
| 4,488,542 | 12/1984 | Helland . |
| 4,615,338 | 10/1986 | Ilizarov et al. . |
| 4,978,348 | 12/1990 | Ilizarov ................................. 606/57 |
| 5,074,866 | 12/1991 | Sherman et al. ....................... 606/56 |
| 5,358,504 | 10/1994 | Paley et al. ............................. 606/56 |
| 5,486,176 | 1/1996 | Hildebrand et al. ................... 606/71 |

*Primary Examiner*—David O. Reip
(74) *Attorney, Agent, or Firm*—Harness, Dickey & Pierce, P.L.C.

(57) ABSTRACT

An external fixator for securing a bone through a first bone screw connected to a first portion of the bone and a second bone screw connected to a second portion of the bone. The external fixator includes a first bone screw clamping assembly for receiving the first bone screw and a second bone screw clamping assembly for receiving the second bone screw. The external fixator additionally includes an angular correction module connecting the first and second bone screw clamping assemblies. The angular correction module includes a first element and a second element coupled to allow articulation of the first bone screw clamping assembly relative to the second bone screw clamping assembly about a center of rotation spaced from the module.

18 Claims, 7 Drawing Sheets

EXTERNAL FIXATOR INCLUDING AN ANGULAR CORRECTION MODULE AND RELATED METHOD

BACKGROUND OF THE INVENTION

1. Field of the Invention

The present invention relates generally to the external fixation of bones. More particularly, the present invention relates to an angular correction module for an external fixator which facilitates the gradual angular correction of bone deformities and malunions. More specifically, but without restriction to the particular embodiment and/or use which is shown and described for purposes of illustration, the present invention relates to a method and apparatus incorporating a module for articulating a first bone screw clamping assembly relative to a second bone screw clamping assembly about a center of rotation spaced from the module.

2. Discussion of the Related Art

In various orthopedic surgical procedures, it is necessary to secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed in the desired position during bone regeneration.

Various external fixation devices for the repair of traumatized bone are known. For example, U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is necessary to engage two bone portions in a fixed relationship and angularly adjust the two bone portions relative to each other. The need for making such an adjustment is frequently the result of bone deformity. Such bone deformities may result from congenital defects including but not limited to Blount's Disease, Tibia Vara, Paget's Disease and Hypophosphatemic Rickets. Angular adjustment of bone portions may also be required as a result of post-traumatic applications, such as the correction of bone malunions.

Other known devices are available for the correction of bone deformities and malunions. For example, the various products manufactured by Orthofix S.r.l. include a fixator having an elongated main body pivotally attached to a T-clamp. The T-clamp attaches to a plurality of bone pins. This fixator further includes a removable compression-distraction unit for angular correction of a bone. The compression-distraction unit attaches to the main body and the T-clamp. Through compression and distraction the unit functions to pivot the T-clamp relative to the main body, and thereby angularly correct the bone.

While the fixators specifically for correcting bone deformities and malunions of the type described above may have proven acceptable for certain applications, such fixators are nevertheless susceptible to improvements that may enhance their performance of the fixator. In this regard, known devices for external bone fixation are typically not suitable for articulating a first bone screw clamping assembly relative to a second bone screw clamping assembly about a center of rotation passing through an axis of the bone.

SUMMARY OF THE PRESENT INVENTION

An advantage of the present invention is the provision of a method and apparatus for the external fixation of bone which allows the rate of angular correction of bone deformities and malunions to be easily and more accurately controlled.

Another advantage of the present invention is the provision of a method and apparatus for the external fixation of bone in which an accurate correlation can be made between movement of a drive unit and the degrees of corrective angulation to a bone.

Another advantage of the present invention is the provision of a method and apparatus for the external fixation of bone in which gradual angular corrections can be made to a bone, as opposed to acute angular corrections.

Another advantage of the present invention is the provision of a method and apparatus for angularly correcting a bone which eliminates the nuisance of locking and unlocking a mechanism before and after angular adjustments can be made.

A more specific advantage of the present invention is the provision of a method and apparatus for the external fixation of bone incorporating an angular correction module for articulating a first bone screw clamping assembly relative to a second bone screw clamping assembly about an axis spaced from the correction module.

A related advantage of the present invention is the provision of a method and apparatus for the external fixation of bone incorporating an angular correction module for articulating a first bone screw clamping assembly relative to a second bone screw clamping assembly about an axis intersecting a longitudinal axis of the bone.

Another specific advantage of the present invention is the provision of a method and apparatus for the external fixation of bone in which corrective angulation of a bone is obtained through operation of a worm gear.

In one form, the present invention provides an apparatus for external fixation of a bone. The apparatus includes a first bone screw and a second bone screw. The first bone screw is adapted to be connected to a first portion of the bone. The second bone screw is adapted to be connected to a second portion of the bone. A first bone screw clamping assembly receives the first bone screw. A second bone screw clamping assembly receives the second bone screw. An angular correction module connects the first and second bone screw clamping assemblies. The module includes first and second elements coupled to allow articulation of the first bone screw clamping assembly relative to the second bone screw clamping assembly about an axis of rotation. The axis of rotation is spaced from the module.

In another form, the present invention provides a method for adjustably securing a first bone portion to a second bone portion with a first bone screw engaged with the first bone portion and a second bone screw engaged with the second bone portion. The method includes the general steps of forming a first bone screw clamping assembly, forming a second bone screw clamping assembly, and interconnecting the first bone screw clamping assembly and the second bone screw clamping assembly with an angular correction module. The method additionally includes the general steps of connecting the first bone screw to the first bone screw clamping assembly and connecting the second bone screw to the second bone screw clamping assembly. The method further includes the general step of articulating the angular correction module to rotate the first bone screw clamping assembly relative to the second bone screw clamping assembly about an axis of rotation spaced from the angular correction module.

Additional advantages and features of the present invention will become apparent from the following description and appended claims, taken in conjunction with the accompanying drawings.

DETAILED DESCRIPTION OF THE PRESENT INVENTION

The following description of the preferred embodiment of the present invention is merely exemplary in nature and is in no way intended to limit the scope of the present invention or its application or uses.

Figure 1:
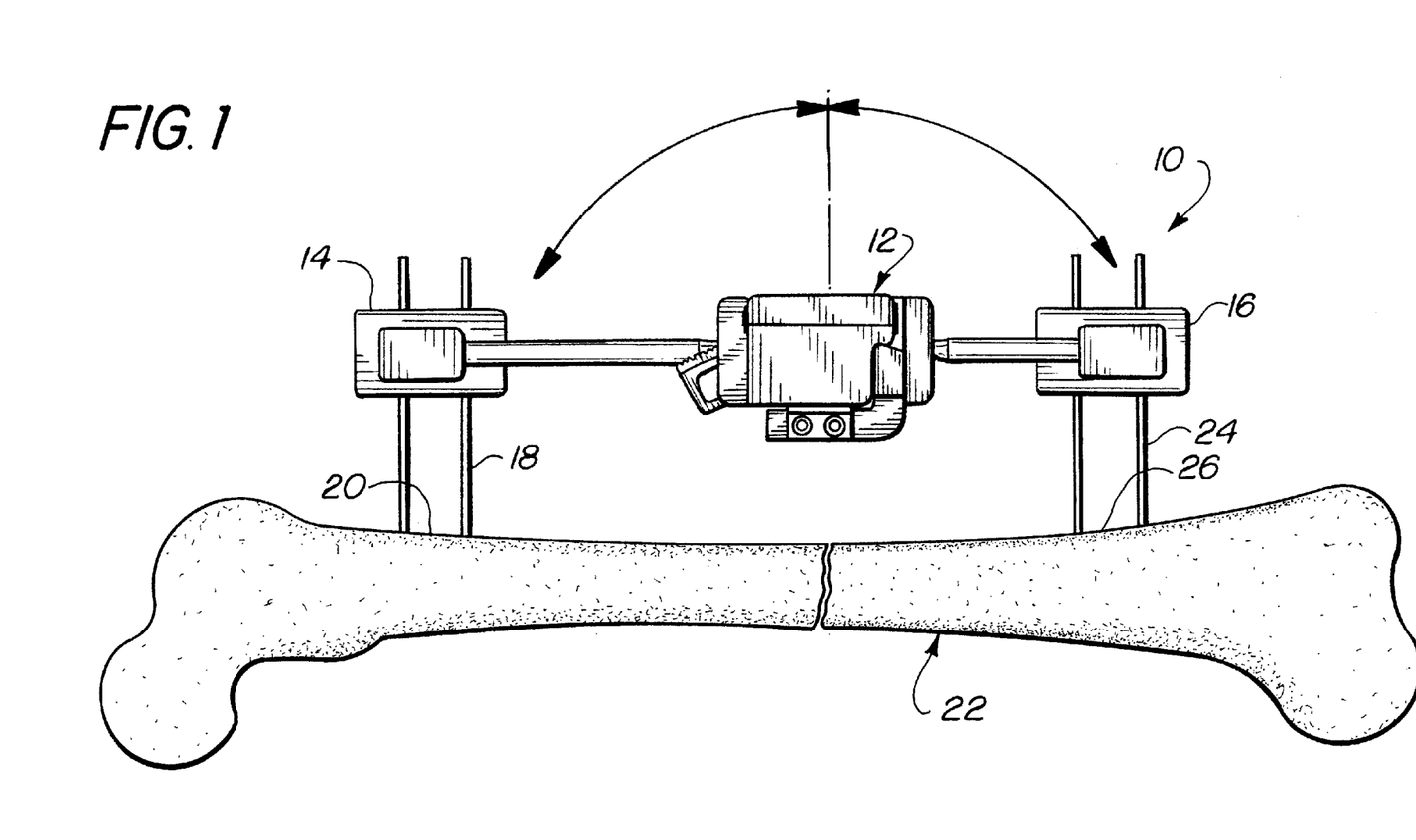
FIG. 1 is a side view of an external fixator constructed in accordance with the teachings of a preferred embodiment of the present invention to include an angular correction module, the external fixator shown in a first construction and shown operatively associated with a human bone.
Figure 2:
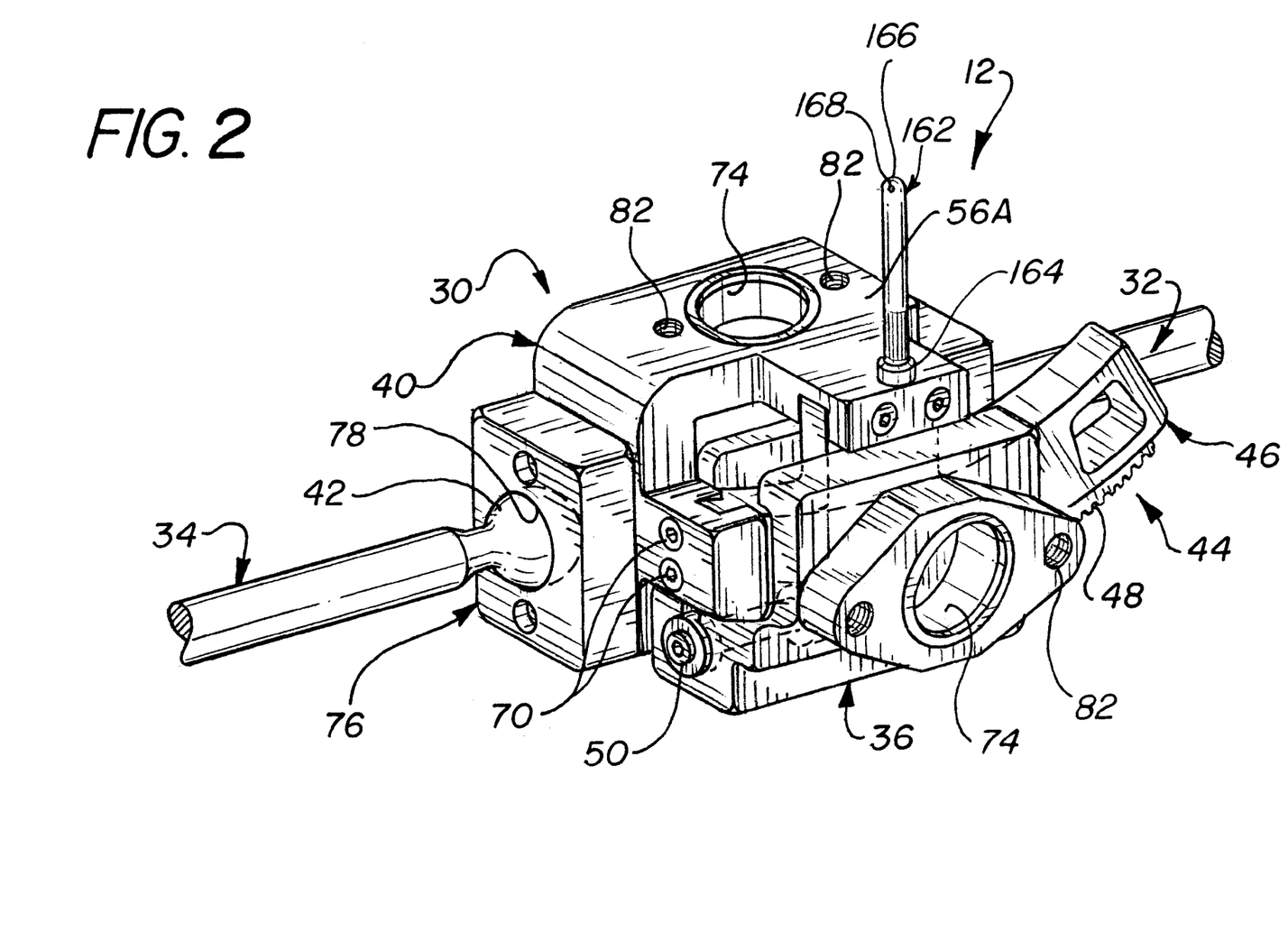
FIG. 2 is an enlarged perspective view of the angular correction module and first and second support arms of the preferred embodiment of the present invention shown in the first construction of FIG. 1.
Figure 3:
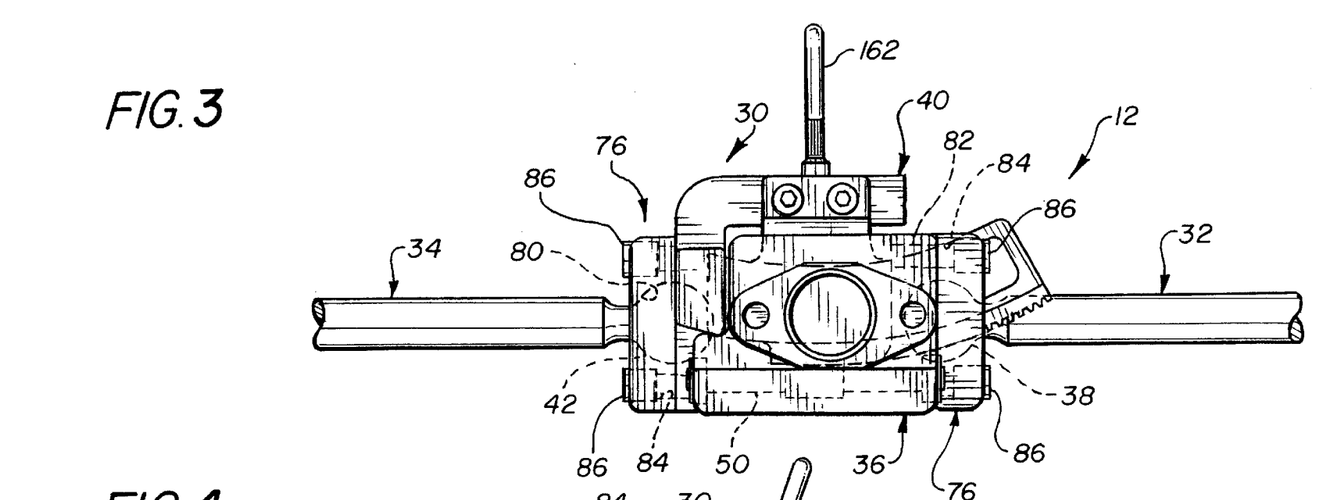
FIG. 3 is an enlarged side view of the angular correction module and first and second support arms of the present invention.
Figure 4:
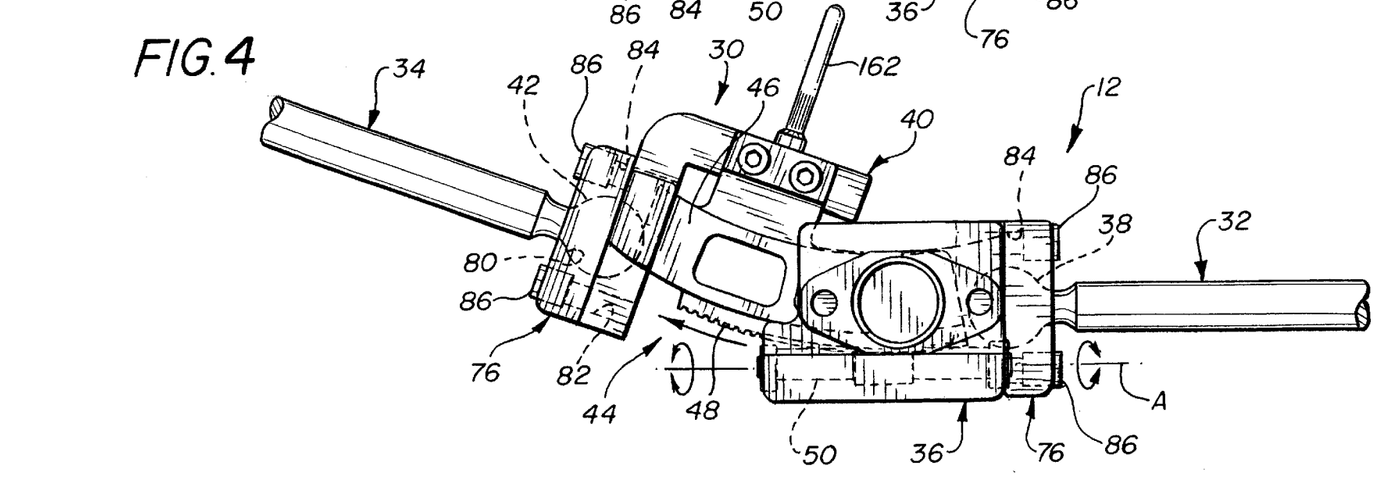
FIG. 4 is a side view similar to FIG. 3, illustrated with the angular correction module articulated from the orientation shown in FIG. 3.

Referring to FIG. 1, an apparatus for external fixation 10 is shown to include an angular correction module 12 constructed in accordance with the teachings of a preferred embodiment of the present invention. In addition to the angular correction module 12, the apparatus 10 is shown to generally include a first bone screw clamping assembly 14 and a second bone screw clamping assembly 16. The first bone screw clamping assembly 14 is used to receive at least one bone screw 18 adapted to engage a first portion 20 of a bone 22 The second bone screw clamping assembly 16 is used to receive at least one bone screw 24 adapted to engage a second portion 26 of the bone 22. As will become apparent below, the module 12 functions to allow articulation of the first bone screw clamping assembly 14 relative to the second bone screw clamping assembly 16. As a result, the first bone portion 20 is angularly adjusted relative to the second bone portion 26 about an axis of rotation.

The principal focus of the present invention relates to the construction and operation of the angular correction module 12. In this regard, it will be understood that the first and second bone screw clamping assemblies 14 and 16 may be of any suitable configuration for interconnecting the module 12 with the first and second bone portions 20 and 26 through the bone screws 18 and 24, respectively. For purposes of fully describing the exemplary embodiment illustrated throughout the drawings, the first and second clamping assemblies 14 and 16 will be more fully discussed below.

With continued reference to the environmental view of FIG. 1 and additional reference to FIGS. 2–6, the angular correction module 12 of the present invention will be further detailed. The angular correction module 12 is shown operatively associated with first and second support arms 32 and 34. The first and second support arms 32 and 34 function to interconnect the angular correction module 12 with the bone screw clamping assemblies 14 and 16, respectively. A first construction of the angular correction module 12 is illustrated in FIGS. 1–4. A second construction of the angular correction module 12, in which the first and second support arms 32 and 34 are alternatively mounted to the angular correction module 12, is shown in FIGS. 6A and 6B.

The angular correction module 12 includes a first element or member 36 for receiving an end 38 of the first support arm 32. The angular correction module 12 further includes a second element or member 40 for receiving an end 42 of the second support arm 34. To provide means for articulating the first bone screw clamping assembly 14 relative to the second bone screw clamping assembly 16, the angular correction module includes a drive mechanism 44. The drive mechanism 44 is preferably gear driven and is shown in the exemplary embodiment to include an arcuate gear segment 46 defining a plurality of teeth 48. The drive mechanism 44 further includes a threaded member or worm 50 threadably engaged with the teeth 48 of the gear segment 46. In the exemplary embodiment, the threaded member 50 is carried by the first member 36 of the angular correction module 12 and the arcuate gear segment 46 is carried by the second member 40 of the angular correction module 12.

The drive mechanism 44 allows the rate of angular correction of bone deformities and malunions to be easily and more accurately controlled. In addition, accurate correlation can be made between movement of the worm 48 and the degree of corrective angulation to the bone. Furthermore, the drive mechanism 44 allows for gradual angular corrections to be made to the bone, as opposed to acute angular corrections, and eliminates the nuisance of locking and unlocking a mechanism before and after angular adjustments are made.

Figure 5A:
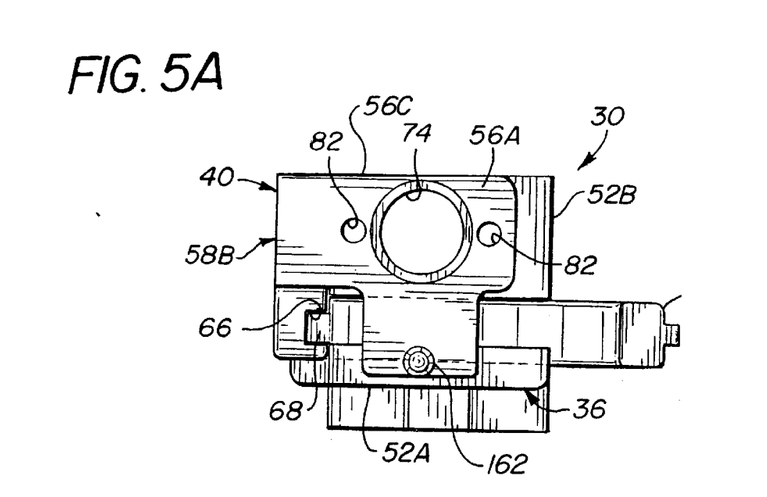
FIGS. 5A–5D further illustrate the angular correction module of the present invention.
Figure 5B:
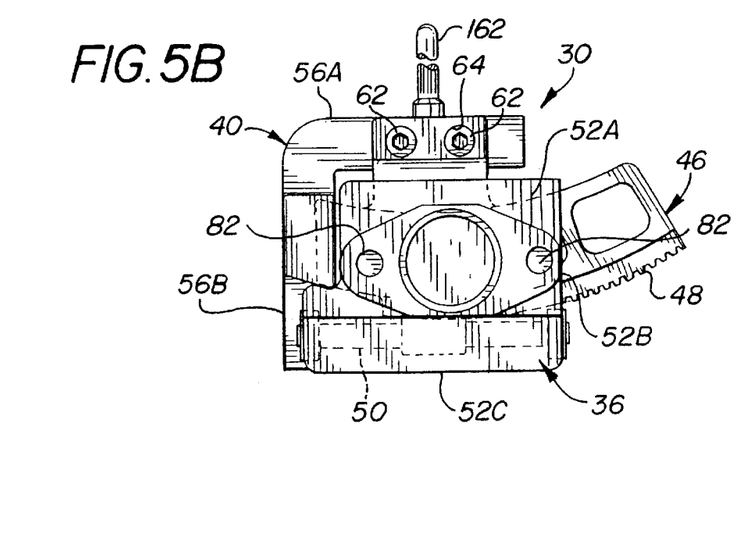
Figure 5C:
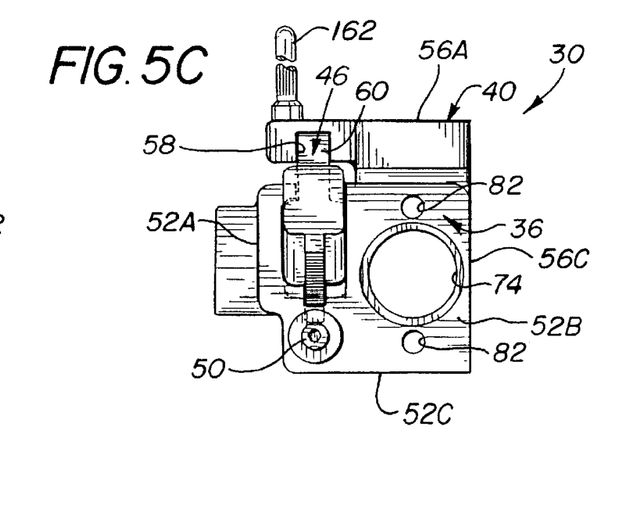
Figure 5D:
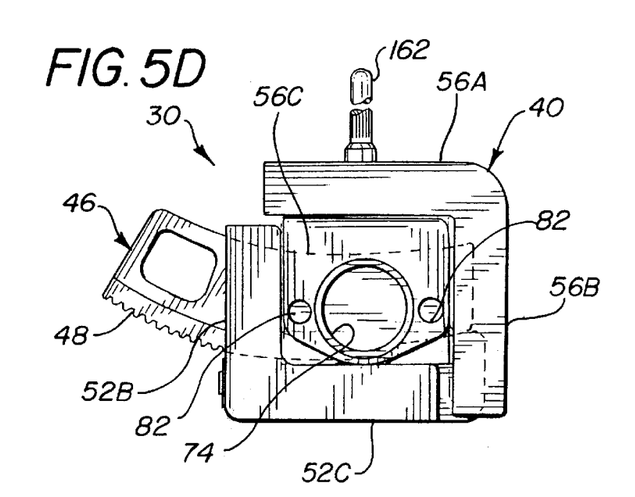

In the exemplary embodiment illustrated, the first member 36 of the angular correction module 12 includes three mutually perpendicular sides 52A, 52B and 52C (identified in FIGS. 5A–5C). The worm 50 is disposed within an aperture proximate the intersection of the side 52A and the side 52C. Rotation of the threaded member 50 about its axis A (identified in FIG. 4) serves to advance the arcuate gear segment 46 relative to the worm 50 through a sweeping path.

The second member 40 of the angular correction module 12 similarly includes first and second mutually perpendicular sides 56A, 56B, and 56C. The side 56A defines a channel 58 which receives a mounting portion 60 of the arcuate gear segment 46. A pair of threaded members 62 pass through the aperture 64 in the side 56A and engage the mounting portion 60. In a similar manner, the side 56B defines a channel 66 for receiving an end 68 of the arcuate gear segment 46. A pair of fasteners 70 (shown in FIG. 2) pass through apertures in the side 56B and engage the end 68 of the arcuate gear segment 46.

To provide means for mounting the support arms 32 and 34 to the first and second members 36 and 38, respectively, the first and second members 36 and 40 both are formed to include a plurality of mounting apertures 74. The apertures 74 allow both the first and second members 36 and 38 to selectively receive one of the first and second support arms 32 and 34 in one of three mutually perpendicular orientations. In the exemplary embodiment illustrated, the ends 38 and 42 of the first and second support arms 32 and 34, respectively, are spherical. The mounting apertures 74 are sized slightly smaller than the spherical ends 38 and 42 of the support arms 32 and 34. A clamping plate 76 is used to adjustably and selectively interconnect the support arms 32 and 34 with the angular correction module. The clamping plates 76 each include an aperture 78 for receiving one of the support arms 32 or 34 and defining an arcuate recess 80 for matingly receiving a portion of the spherical end 38 or 42.

To secure the mounting plates 76 to one of the first and second members 36 and 40, each of the apertures 74 is associated with a pair of threaded holes 82. The threaded holes 82 align with a pair of holes 84 provided in each of the mounting plates 76. The aligning holes 82 and 84 receive threaded fasteners 86. Loose engagement of the threaded fasteners 86 with the holes 82 permits universal adjustment of the spherical ends 38 and 42 relative to the angular correction module 12. Upon tightening of the fasteners 86, relative movement between the spherical ends 38 and 42 and the angular correction module 12 is arrested.

In a first construction shown in FIGS. 1–4, the spherical end 38 of the first support arm 32 is partially received within the aperture 74 provided in the side 52B of the first member 36. The spherical end 42 of the second arm 34 is received within the aperture 74 provided in the side 56B of the second member 40. In this first construction, when the angular correction module 12 is articulated, the first clamping assembly 14 rotates relative to the second clamping assembly 16 about a center of rotation B spaced from the angular correction module 12. This allows the surgeon to articulate the bone portions 20 and 26 relative to one another about an axis of rotation passing through the bone 22. Such an arrangement permits correction of angulation at the site of a deformity, for example, within the bone 22 with the center of rotation not in the correction module 12, but within the bone 22.

Figures 6A, 6B:
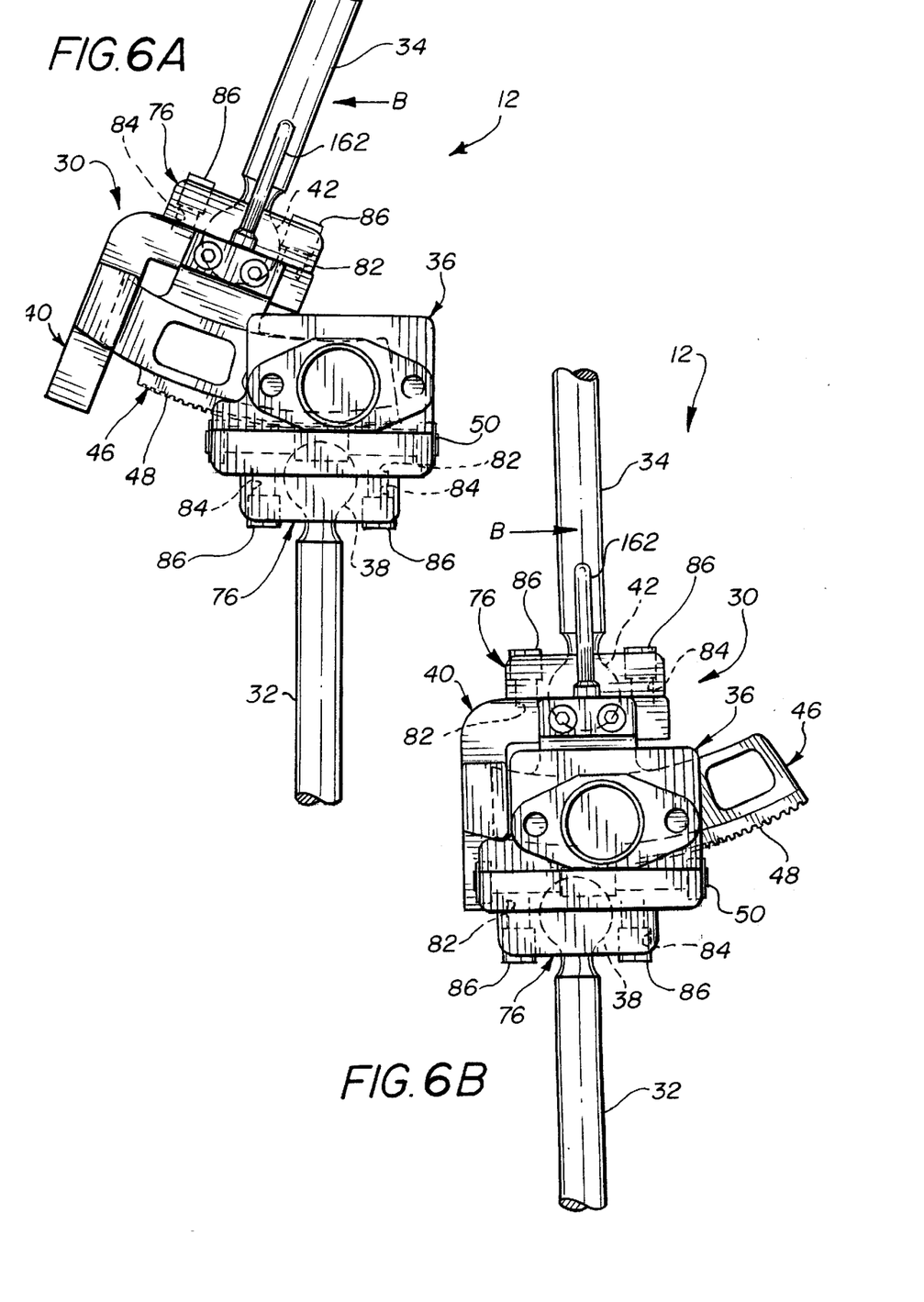
FIGS. 6A and 6B are side views of the angular correction module and the first and second support arms of the present invention shown in a second construction.

In a second construction shown in FIGS. 6A and 6B, the spherical end 38 of the first support arm 32 is partially received within the mounting aperture 74 provided in the side 52C of the first member 36. The spherical end 42 of the second support arm 34 is received within the mounting aperture 74 provided in the side 56A of the second member 40. In the second construction, when the angular correction module 12 is articulated, the first clamping assembly 14 rotates relative to the second clamping assembly 16 about a center of rotation C, again spaced from the angular correction module 12. The second construction permits oblique plane conformities through translational correction, for example.

In a third construction (not specifically shown with the first and second support arms 32 and 34), the correction module 12 can be used for rotational correction of the bone 22. In such a third construction, the spherical end 38 of the first support arm 32 is partially received within the mounting aperture 74 provided in the side 52A of the first member 36. The spherical end 42 of the second support arm 34 is received within the mounting aperture 74 provided in the side 56C of the second member 40. Advantageously, rotational correction can be accomplished along the axis of the bone without any displacement.

The exemplary bone screw clamping assemblies 14 and 16 will be described in greater detail with reference to FIGS. 1 and 7. It will be understood that the first and second bone screw clamping assemblies 14 and 16 are substantially identical. Thus, while this detailed description will be primarily directed to the construction and operation of the first bone screw clamping assembly 14, a complete understanding of the second bone screw clamping assembly 16 will be apparent therefrom. Again, it will be noted that any suitable clamping assembly may be used with the angular correction module 12 of the present invention.

Figure 7:
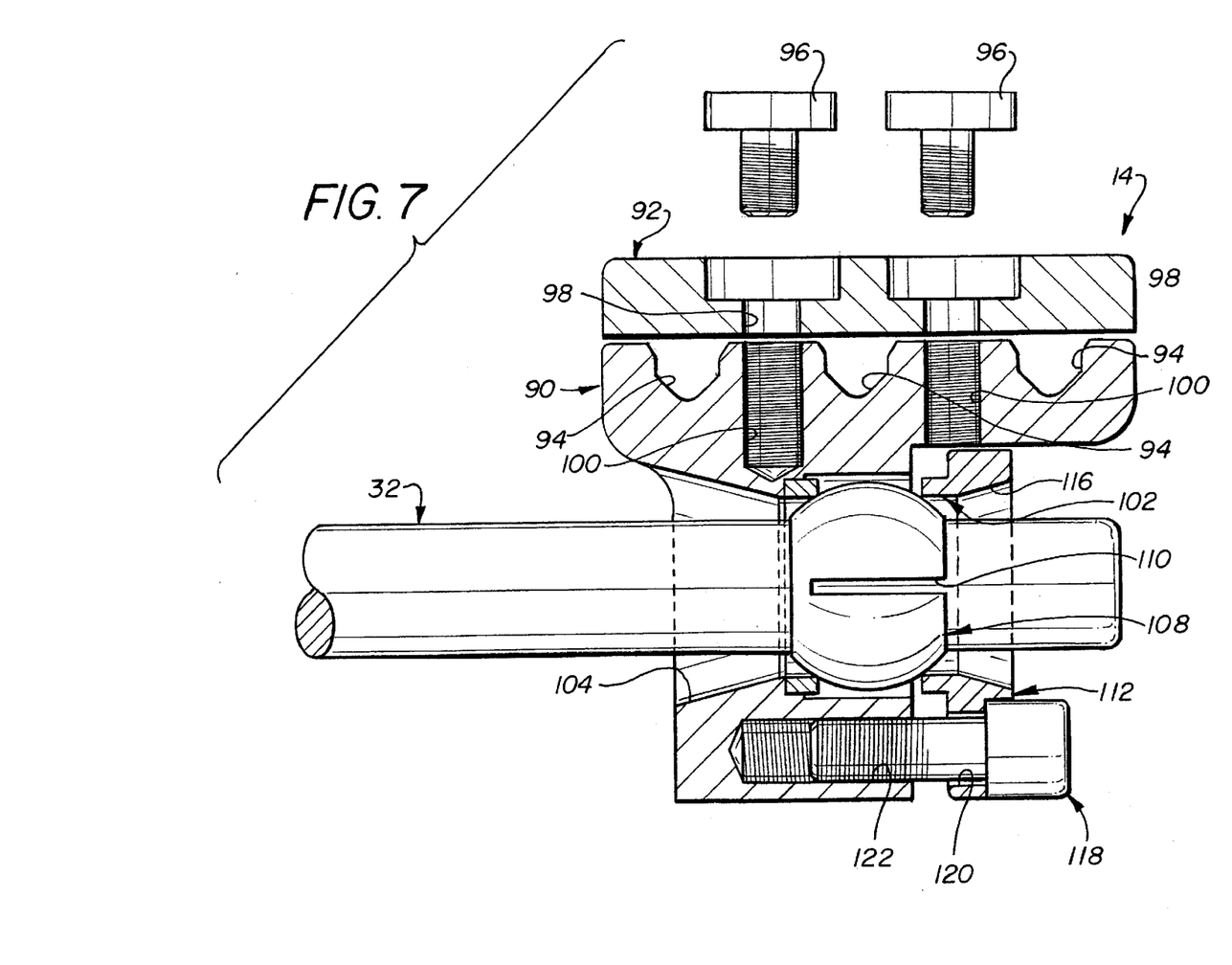
FIG. 7 is a cross-sectional view of one of the bone screw clamping assemblies shown in FIG. 1 operatively associated with one of the support arms.

With particular reference to FIG. 7, the first bone screw clamping assembly 14 is illustrated to generally include a base portion 90 and a cover portion 92. The base portion 90 preferably serves to receive two bone screws 18 in two of a plurality of grooves 94. The cover portion 92 serves to secure the bone screws 18 within the grooves 94.

The cover portion 92 of the first bone screw clamping 14 is secured to the base portion 90 by means of two screws 96. To accommodate these screws 96, the cover portion 92 of the bone screw clamping assembly 14 includes two apertures 98 which align with corresponding apertures 100 in the base portion 90 of the bone screw clamping assembly 14. Accordingly, upon secured threaded engagement of the screws 96 within the apertures 98 and 100, the cover portion 92 of the bone screw clamping assembly 14 may be secured to the base portion 90.

The base portion 90 of the bone screw clamping assembly 14 is illustrated to include a channel 102 passing therethrough for receiving the first support arm 32. The channel 102 includes a first end 104 which outwardly tapers. Disposed within a second end 106 of the channel 102 is a movable collet 108 of spherical configuration. The collet 108 is slotted at 110 to permit collet closure about the first support arm 32. Acting on the collet 108 is a compression element 112. The compression element 112 defines an aperture 114 having an outwardly tapering conical end 116. The compression element 112 is interconnected to the base portion 90 of the bone screw clamping assembly 14 through a threaded fastener 118 which passes through an aperture 120 provided in the compression element 112 and threadably engages an aperture 122 in the base portion 90 of the bone screw clamping assembly 14. Prior to tightening of the fastener 118, the bone screw clamping assembly 14 can be adjusted relative to the first support arm 32. The end 104 of the aperture 102 and the end 116 of the compression element 112 permit angular adjustment of the bone screw clamping assembly 14 relative to the first support arm 32. Upon tightening of the fastener 118, the collet 108 is compressed and relative movement between the bone screw clamping assembly 14 and the first support arm 32 is arrested.

Figure 8:
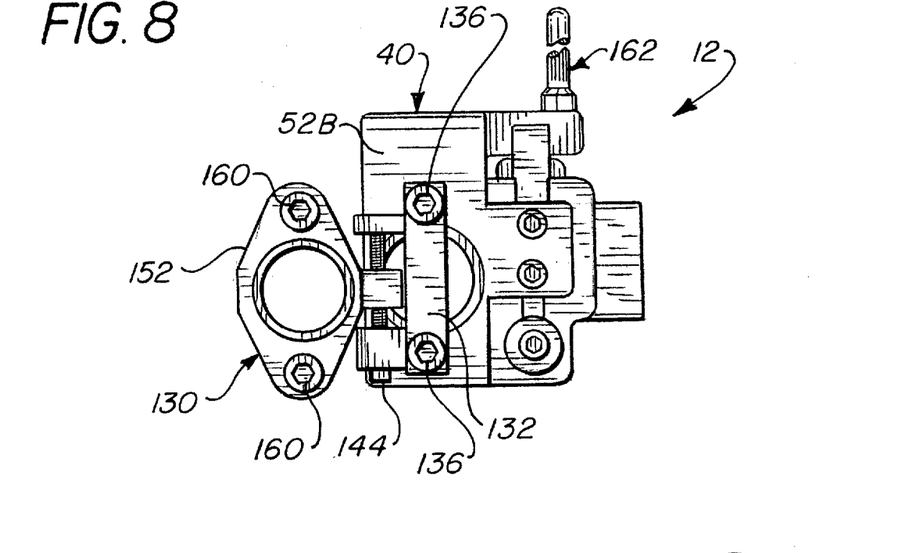
FIG. 8 is a left side view of the angular correction module of the present invention illustrated with an alternative support arm mounting arrangement attached thereto.
Figure 9:
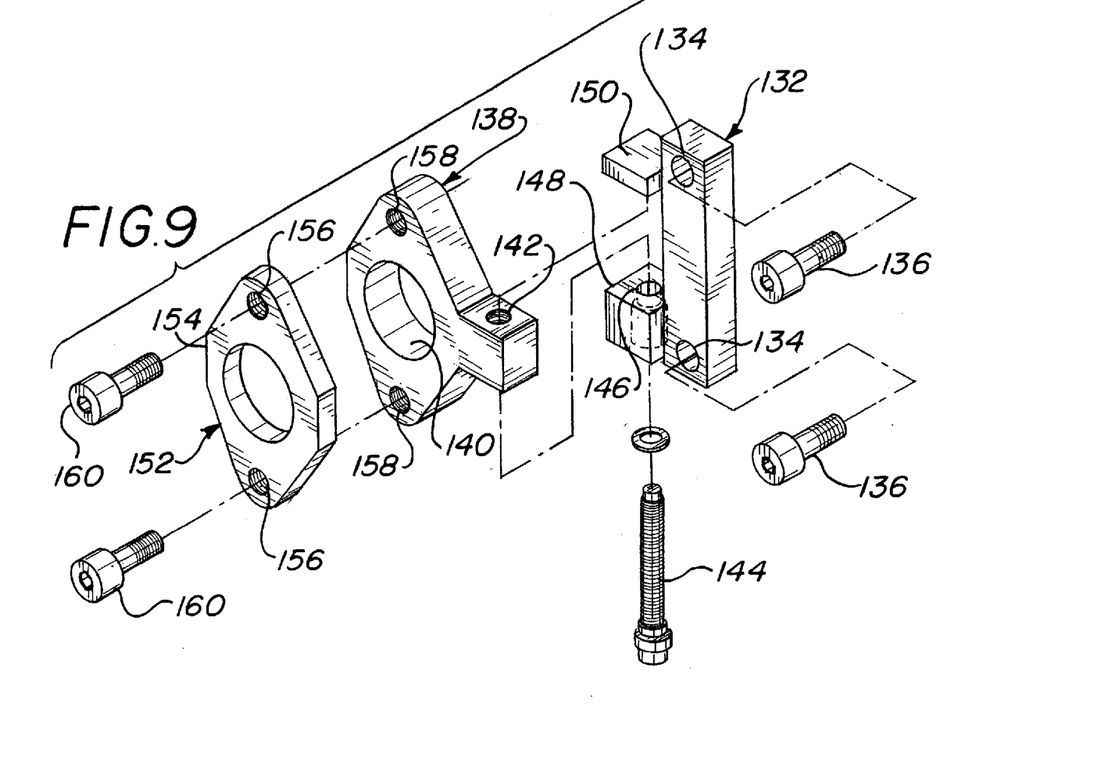
FIG. 9 is an enlarged and exploded perspective view of the alternative support arm mounting arrangement shown in FIG. 8.

Turning now to FIGS. 8 and 9, an alternative support arm mounting arrangement 130 is illustrated. As will be appreciated more fully below, the mounting arrangement 130 is operative for linearly translating the spherical end 42 of one of the first and second support arms 32 and 34 relative to the angular correction module 12. In the exemplary use arrangement shown in FIG. 8, the mounting arrangement 130 is shown operatively attached to the side 52B of the second member 40. However, it will be readily appreciated that the mounting arrangement 130 can be removably secured to the correction module 12 in various other positions.

The mounting arrangement 130 includes a mounting portion 132 adapted to be directly secured to the correction module 12. The mounting portion 132 defines a pair of apertures 134 for receiving fasteners 136. The fasteners 136 engage the threaded holes 82 in the side 52B. The mounting arrangement 130 further includes a support member receiving portion 138 which defines an aperture 140 for partially receiving the spherical end 42 of one of the first and second support arms 32 and 34. To provide means for linearly translating the support arm mounting portion 138 relative to the correction module 12, the support arm mounting portion defines a threaded aperture 142. The threaded aperture 142 receives a threaded member or worm 144 which is rotatably carried by the mounting portion 132. In this regard, the worm 144 passes through an aperture 146 provided in a first flange 148 and an end of the worm 144 is rotatably received in an aperture (not specifically shown) provided in a second flange 150. Rotation of the worm 144 in a first direction causes linear translation of the support arm mounting portion 138 in an upward direction (as shown in FIG. 8). Conversely, rotation of the worm 144 in a second, opposite direction causes linear translation of the support arm mounting portion 138 in a downward direction.

The mounting aperture 140 of the support arm mounting portion 138 is sized slightly smaller than the spherical ends 38 and 42 of the support arms 32 and 34. A clamping plate 152 is used to adjustably and selectively interconnect one of the support arms 32 and 34 with the angular correction module 12. The clamping plate 152 defines an aperture 154 for receiving a portion of the spherical end 38 or 42. To secure the mounting plate 152 to the mounting portion 138, the mounting plate 152 includes a pair of apertures 156 which align with a pair of apertures 158 provided in the mounting portion 138. The aligning apertures 156 and 158 threadably receive threaded fasteners 160. Loose engagement of the threaded fasteners 160 with the apertures 156 and 158 permits universal movement of the spherical end 32 or 42 relative to the angular correction module 12. Upon tightening of the fasteners 160, relative movement between the spherical end 32 or 42 and the angular correction module 12 is arrested.

In the exemplary embodiment, the correction module 12 is illustrated to include a locating element 162. In desired applications, the locating element 162 can be used to facilitate alignment of the correction module 12 with the bone 22. The locating element 162 includes a lower end 164 which threadably engages an aperture (not specifically shown) provided in side 56A of the second member 40. An upper end 166 of the locating element includes a small aperture 168 which may be used to receive a k-wire in a manner well known in the art.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for external fixation of a bone through a first bone screw connected to a first portion of the bone and a second bone screw connected to a second portion of the bone, the apparatus comprising:

a first bone screw clamping assembly for receiving the first bone screw;

a second bone screw clamping assembly for receiving the second bone screw; and an angular correction module connecting the first and second bone screw clamping assemblies, said angular correction module including a first element and a second element coupled to allow articulation of said first bone screw clamping assembly relative to said second bone screw clamping assembly about a center of rotation, said center of rotation being spaced from said module;

wherein at least one of said first and second bone screw clamping assemblies includes a generally spherical end providing universal adjustment between said module and said at least one of said first and second bone screw clamping assemblies.

2. The apparatus for external fixation of a bone of claim 1, wherein said angular correction module includes a gear driven arrangement for articulating said first element relative to said second element.

3. The apparatus for external fixation of a bone of claim 2, wherein said gear driven arrangement includes a threaded element rotatably carried by one of the first and second elements meshingly engaged with a gear segment carried by the other of the first and second elements.

4. The apparatus for external fixation of a bone of claim 3, wherein said gear segment is an arcuate gear segment.

5. The apparatus for external fixation of a bone of claim 4, wherein said arcuate gear segment includes a center of curvature defining said center of rotation.

6. The apparatus for external fixation of a bone of claim 1, wherein both of said first and second bone screw clamping assemblies include a generally spherical end adjustably secured to said module.

7. An apparatus for external fixation of a bone through a first bone screw connected to a first portion of the bone and a second bone screw connected to a second portion of the bone, the apparatus comprising:

a first bone screw clamping assembly for receiving the first bone screw;

a second bone screw clamping assembly for receiving the second bone screw; and an angular correction module interconnecting said first and second bone screw clamping assemblies, said angular correction module including a first element coupled to a second element to allow for articulation of said first bone screw clamping assembly relative to said second bone screw clamping assembly about a center of rotation, said first and second elements each adapted to selectively receive one of said first and second bone screw clamping assemblies in one of two mutually perpendicular orientations.

8. The apparatus for external fixation of a bone of claim 7, wherein said center of rotation is spaced from said module.

9. The apparatus for external fixation of a bone of claim 7, wherein said first element includes a pair of mutually perpendicular surfaces adapted to selectively receive an end of said first bone screw clamping assembly.

10. The apparatus for external fixation of a bone of claim 9, wherein said angular correction module further includes a clamping member for securing said first bone screw clamping assembly to one of said pair of mutually perpendicular surfaces.

11. The apparatus for external fixation of a bone of claim 10, wherein said clamping member permits universal movement between said end of said first bone screw clamping assembly and said first element.

12. The apparatus for external fixation of a bone of claim 9, wherein said end of said first bone screw clamping assembly is a spherical end.

13. The apparatus for external fixation of a bone of claim 12, wherein each of said mutually perpendicular surfaces of said first element includes an aperture adapted to selectively and partially receive said spherical end of said first bone screw clamping assembly.

14. The apparatus for external fixation of a bone of claim 12, wherein said clamping member partially defines an arcuate recess mating with a portion of said spherical end of said first bone screw clamping assembly.

15. A method for adjustably securing a first bone portion to a second bone portion with a first bone screw engaged with the first bone portion and a second bone screw engaged with the second bone portion, the method comprising the steps of:

forming a first bone screw clamping assembly;

forming a second bone screw clamping assembly;

interconnecting said first bone screw clamping assembly and said second bone screw clamping assembly with an angular correction module;

connecting the first bone screw to said first bone screw clamping assembly;

connecting the second bone screw to said second bone screw clamping assembly; and articulating said angular correction module to rotate said first bone screw clamping assembly relative to said second bone screw clamping assembly about an axis of rotation passing through the bone.

16. The method of claim 15, wherein the step of interconnecting said first bone screw clamping assembly and said second bone screw clamping assembly with an angular correction module includes the step of connecting an end of said first bone screw clamping assembly to said angular correction module to allow universal movement therebetween.

17. The method of claim 15, wherein the step of articulating said angular correction module includes the steps of:

rotatably mounting a threaded member to a first element of said angular correction module;

mounting a gear segment to a second element of said angular correction module;

meshingly engaging said threaded member and said gear segment; and rotating said threaded member to articulate said first element relative to said second element.

18. The method of claim 17, wherein the step of mounting a gear segment to a second element of said angular correction module includes the step of mounting an arcuate gear segment to said second element of said angular correction module.

* * * * *